United States Patent [19]

Daigle et al.

[11] 3,932,390

[45] Jan. 13, 1976

[54] 2-THIA-1,3,5-TRIAZA-7-PHOSPHAADAMANTANE 2,2-DIOXIDE

[75] Inventors: Donald J. Daigle, New Orleans; Armand B. Pepperman, Jr., Metairie; Gordon J. Boudreaux, New Orleans, all of La.

[73] Assignee: The United States of America as represented by the Secretary of Agriculture, Washington, D.C.

[22] Filed: Apr. 29, 1975

[21] Appl. No.: 572,802

Related U.S. Application Data

[62] Division of Ser. No. 471,516, May 20, 1974, Pat. No. 3,899,618.

[52] U.S. Cl............... 260/243 R; 117/136; 252/8.1; 106/15 FP; 8/183
[51] Int. Cl.².......................................... C07D 285/00
[58] Field of Search ............................... 260/243 R

[56] References Cited

UNITED STATES PATENTS

| | | | |
|---|---|---|---|
| 3,734,684 | 5/1973 | Donaldson | 8/183 |
| 3,737,284 | 6/1973 | O'Brein et al. | 8/183 |
| 3,745,191 | 7/1973 | Daigle et al. | 260/606.5 |

*Primary Examiner*—John M. Ford
*Attorney, Agent, or Firm*—M. Howard Silverstein; Max D. Hensley

[57] ABSTRACT

2-Thia-1,3,5-triaza-7-phosphaadamantane 2,2-dioxide was prepared. The phosphine was converted to the phosphine oxide derivative by reaction with hydrogen peroxide and the methyl phosphonium iodide derivative of the phosphene was prepared by reaction with methyl iodide.

3 Claims, No Drawings

2-THIA-1,3,5-TRIAZA-7-PHOSPHAADAMANTANE 2,2-DIOXIDE

This is a division of application Ser. No. 471,516, filed May 20, 1974, now U.S. Pat. No. 3,899,618.

This invention relates to a hexamethylenetetramine analog containing sulfur and phosphorus. More specifically this invention relates to 2-thia-1,3,5-triaza-7-phosphaadamantane 2,2-dioxide and its derivatives, 2-thia-1,3,5-triaza-7-phosphaadamantane 2,2,7-trioxide and 2-thia-1,3,5-triaza-7-methyl-7-phosphonia-adamantane 2,2-dioxide iodide which are useful as flame retardants for cellulosic textiles and to methods of their preparation.

The main object of the instant invention is to disclose the compound 2-thia-1,3,5-triaza-7-phosphaadamantane produced by processes of the instant invention.

A second object of the instant invention is to disclose the derivatives of 2-thia-1,3,5-triaza-7-phosphaadamantane 2,2-dioxide, 2-thia-1,3,5-triaza-7-phosphaadamantane 2,2,7-trioxide and 2-thia-1,3,5-triaza-7-methyl-7-phosphoniaadamantane 2,2-dioxide iodide.

Searching the prior art we find that the process for the preparation of tris(aminomethyl)phosphine is conducted by reacting a secondary amine with tris(hydroxymethyl)phosphine by itself or in the presence of formaldehyde. [K. A. Petrov, V. A. Parshina, B. A. Orlov, and G. M. Trypine, Zhur. Obshch. Khem., 32, 4017 (1962)]. The prior art also shows that hexamethylenetetramine or a solution of formaldehyde and ammonia can be employed rather than simple amines. [D. J. Daigle, A. B. Pepperman, Jr., and S. L. Vail, Ser. No. 391,189; filed Aug. 24, 1973], now U.S. Pat. No. 3,899,619. In this prior art a phosphine ($C_6H_{12}N_3P$) having the graphic formula can be prepared by reacting tris(hydroxymethyl)phosphine with hexamethylenetetramine, preferably in the presence of formaldehyde.

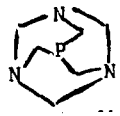

The amine of the present invention differs from those of the prior arts in that hexamethylenetetramine or ammonia and sulfamide is employed rather than secondary amine. Thus, the phosphine of the present invention is of a new type. In the course of the investigation we have found that a phosphine ($C_5H_{10}N_3O_2PS$) having the graphic formula shown below can be prepared by reacting tris(hydroxymethyl)phosphine

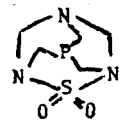

with sulfamide and ammonia or preferably a source of ammonia, hexamethylenetetramine and preferably in the presence of formaldehyde.

In accordance with the present invention the reaction of tris(hydroxymethyl)phosphine with sulfamide and hexamethylenetetramine is carried out by dissolving the rea-ent tris(hydroxymethyl)phosphine in 20% formalin (5–10 times the weight of the reagent) and hexamethylenetetramine and sulfamide added and dissolved in the solution at room temperature. The final solution was allowed to stand at room temperature overnight. This same procedure may be carried out using a solution of ammonia in place of hexamethylenetetramine. The phosphine product was identified by infrared and proton magnetic resonance spectra, and by elemental analysis.

Further, in accordance with the present invention 2-thia-1,3,5-triaza-7-phosphaadamantane 2,2,7-trioxide was prepared by reaction of 2-thia-1,3,5-triaza-7-phosphaadamantane 2,2-dioxide with a peroxide in an appropriate solvent.

In accordance with the present invention 2-thia-1,3,5-triaza-7-methyl-7-phosphoniaadamantane 2,2-dioxide iodide was prepared by reaction of 2-thia-1,3,5-triaza-7-phosphaadamantane 2,2-dioxide with methyl iodide in an appropriate solvent.

These compounds are useful as flame retardants for cellulosic material and also as intermediates for other chemical compounds and polymers. Cotton fabric was made flame retardant by impregnating the fabric with a 15% dimethyl sulfoxide solution of the compound and drying the fabric. The concentration of the flame retardant may be varied above or below 15% depending on the degree of flame retardancy desired.

The following examples illustrate the methods of carrying out the invention and are included for purposes of illustration, not as a limitation thereof.

EXAMPLE 1

Preparation of 2-thia-1,3,5-triaza-7-phosphaadamantane 2,2-dioxide. Tris(hydroxymethyl)phosphine (3.9 g, 80%, 0.025 moles) was dissolved in formalin (20 ml, 40%, 0.267 moles) and water (20 ml). Sulfamide (2.4 g, 0.025 mole) and hexamethylenetetramine (3.5 g, 0.025 mole) were added together and dissolved in the solution at room temperature. The solution heated up slightly and over the next twenty-four hours a precipitate formed. Filtration, dissolution of the solid in 4 successive 30 ml acetone washes and evaporation of the acetone yielded 3.42 g of crude 2-thia-1,3,5-triaza-7-phosphaadamantane 2,2-dioxide (66% yield) [mp 274°–5° (water)].

Anal. Calcd. for $C_5H_{10}N_3O_2PS$: C, 28.98; H, 4.86; N, 20.28; P, 14.95; S, 15.48; mol. wt. 207.2. Found: C, 28.85; H, 4.82; N, 20.26; P, 15.14; S, 15.62; mol. wt. 210.

EXAMPLE 2

Preparation of 2-thia-1,3,5-triaza-7-phosphaadamantane 2,2,7-trioxide. 2-Thia-1,3,5-triaza-7-phosphaadamantane 2,2-dioxide (0.5g, 0.0024 mole) and t-butyl hydroperoxide (70% solution, 0.3 g, 0.0024 mole) were stirred in a 25 ml acetone-25 ethanol solution for 1 hour at room temperature. The solution was filtered to yield 0.5 g of crude 2-thia-1,3,5-triaza-7-phosphaadamantane 2,2,7-trioxide (92% yield) [MP 245°–6° (propanol)].

Anal. Calcd. for $C_5H_{10}N_3O_3PS$: C, 26.90; H, 4.52; N, 18.83; P, 13.87; S, 14.37; mol. wt. 223.2 Found: C, 27.11; H, 4.55; N, 18.98; P, 14.10; S, 14.20; mol. wt. 227.

EXAMPLE 3

Preparation of 2-thia-1,3,5-triaza-7-methyl-7-phosphoniaadamantane 2,2-dioxide iodide. 2-Thia-1,3,5-triaza-7-phosphaadamantane (0.35 g, 0.0017 mole) and methyl iodide (0.3 g, 0.002 mole) were refluxed for 24 hours in a 5 ml chloroform-40 ml ethyl acetate solution. The solution was filtered to yield 0.45 g of crude 2-thia-1,3,5-triaza-7-methyl-7-phosphonia-adamantane 2,2-dioxide iodide (76% yield) [MP 202°–3° (methylethyl acetate)].

Anal: Calcd. for $C_6H_{13}N_3O_2PSI$: C, 20.64; H, 3.75; N, 12.04; P, 8.87; S, 9.19; I, 36.35. Found: 20.82; H, 3.75; N, 12.14; P, 8.90; S, 9.34, I, 36.52.

EXAMPLE 4

A solution of ammonia may be used in place of hexamethylenetetramine to prepare 2-thia-1,3,5-triaza-7-phosphaadamantane 2,2-dioxide. Tris(hydroxymethyl)phosphine (3.9 g, 80%, 0.025 moles) was dissolved in formalin (20 ml, 40%, 0.267 moles) and water (20 ml). Ammonium hydroxide (29% $NH_3$, 1.7 ml, 0.025 moles) was added to the solution at room temperature. Sulfamide (2.4 g, 0.025 mole) was then added and dissolved in the solution at room temperature. The solution heated up slightly and over the next twenty-four hours a precipitate formed. Filtration, dissolution of the solid in 4 successive 30 ml acetone washes and evaporation of the acetone yielded 1.0 g of crude 2-thia-1,3,5-triaza-7-phosphaadamantane (19.3% yield).

EXAMPLE 5

Fabric Treatment: A dimethyl sulfoxide solution containing 15% by weight of 2-thia-1,3,5-triaza-7-phosphaadamantane 2,2-dioxide was applied to 8 oz. cotton sateen fabric by passing through squeeze rolls to an 80% wet pickup and rying for 4 minutes at 90°C. The fabric had a 12% weight gain and was flame retardant.

The fabric treatments were evaluated by a well known rapid evaluation flame retardancy test which consists of cutting a small specimen (about 1 cm. × 7 cm.) of the fabric to be evaluated, placing the specimen above the flame of a kitchen match with the long axis of the fabric specimen at an angle of 180° to the flame, igniting the specimen (if it can ignite), removing the flaming specimen from the flame, and rotating the specimen until the flame is extinguished and recording that angle. (The 0° angle would be where the flame is at the top of the specimen, and the most severe test would be where the flame would be at the bottom. This would be the 180° angle.)

The specimens of Example 1 dod not support combustion upon being submitted to this test, that is, the flame was extinguished at a 135° angle; therefore, they passed the flame retardancy test.

The same results were obtained with fabrics treated in the same manner with compounds prepared as described in examples (2), (3).

We claim:
1. 2-Thia-1,3,5-triaza-7-phosphaadamantane 2,2-dioxide.
2. 2-Thia-1,3,5-triaza-7-phosphaadamantane 2,2,7-trioxide.
3. 2-Thia-1,3,5-triaza-7-methyl-7-phosphoniaadamantane 2,2-dioxide iodide.

* * * * *